United States Patent
Yokota et al.

(10) Patent No.: US 8,961,460 B2
(45) Date of Patent: Feb. 24, 2015

(54) SYRINGE NEEDLE ASSEMBLY AND MEDICATION INJECTION DEVICE

(75) Inventors: Takayuki Yokota, Nakakoma-gun (JP); Yoichiro Iwase, Ashigarakami-gun (JP); Yoshinori Hishikawa, Nakakoma-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 329 days.

(21) Appl. No.: 13/496,168

(22) PCT Filed: Sep. 13, 2010

(86) PCT No.: PCT/JP2010/065743
§ 371 (c)(1),
(2), (4) Date: Mar. 14, 2012

(87) PCT Pub. No.: WO2011/040219
PCT Pub. Date: Apr. 7, 2011

(65) Prior Publication Data
US 2012/0179114 A1    Jul. 12, 2012

(30) Foreign Application Priority Data
Sep. 30, 2009    (JP) .................................. 2009-228547

(51) Int. Cl.
*A61M 5/00*        (2006.01)
*A61M 5/34*        (2006.01)
(Continued)

(52) U.S. Cl.
CPC ............. *A61M 5/347* (2013.01); *A61M 5/3293* (2013.01); *A61M 5/343* (2013.01); *A61M 5/3202* (2013.01);
(Continued)

(58) Field of Classification Search
CPC ................................ A61M 5/34; A61M 5/343
USPC ................... 604/117, 239, 272; 156/293, 423
See application file for complete search history.

(56) References Cited

U.S. PATENT DOCUMENTS 5,215,621 A    6/1993    Awazu et al.
5,222,502 A *  6/1993    Kurose .......................... 600/576
(Continued)

FOREIGN PATENT DOCUMENTS

EP    2 033 673 A1    3/2009
JP    8-000597 A       1/1996
(Continued)

OTHER PUBLICATIONS

International Search Report (PCT/ISA/210) issued on Oct. 12, 2010, by Japanese Patent Office as the International Searching Authority for International Application No. PCT/JP2010/065743.
(Continued)

*Primary Examiner* — Laura Bouchelle
(74) *Attorney, Agent, or Firm* — Buchanan Ingersoll & Rooney PC (57) ABSTRACT

To prevent a coating agent applied to the surface of a needle tube from being infiltrated into the clearance between the needle tube and a needle hub, a device comprises a needle tube that has a needle tip capable of puncturing a living body and that is coated with a coating agent on the surface of a tip-end portion on the side of the needle tip; and a needle hub adapted to hold the needle tube in a state where the needle tip of the needle tube is protruded. The needle hub has a through-hole through which the needle tube is inserted, and a discharge hole extending from the through-hole to the outer surface of the needle hub and adapted to discharge the coating agent infiltrated into the through-hole.

7 Claims, 4 Drawing Sheets

(51) Int. Cl.
*A61M 5/32* (2006.01)
*A61M 5/46* (2006.01)

(52) U.S. Cl.
CPC .................. *A61M 5/329* (2013.01); *A61M 5/46* (2013.01); *A61M 2205/0222* (2013.01); *A61M 2205/0238* (2013.01)
USPC ............................ 604/117; 604/272; 604/239

(56) References Cited

U.S. PATENT DOCUMENTS

| | | |
|---|---|---|
| 2002/0138042 A1 | 9/2002 | Llorach et al. |
| 2003/0050602 A1 | 3/2003 | Pettis et al. |
| 2004/0243165 A1 | 12/2004 | Koike et al. |
| 2007/0118077 A1* | 5/2007 | Clarke et al. .................. 604/117 |
| 2007/0149924 A1 | 6/2007 | Marsh |
| 2007/0149944 A1* | 6/2007 | Tashiro et al. ................ 604/413 |

FOREIGN PATENT DOCUMENTS

| | | |
|---|---|---|
| JP | 9-108351 A | 4/1997 |
| JP | 2004-525687 A | 8/2004 |
| JP | 2005-527249 A | 9/2005 |
| JP | 2006-116163 A | 5/2006 |
| JP | 2008-043583 A | 2/2008 |
| JP | 2008-307423 A | 12/2008 |
| JP | 2009-511192 A | 3/2009 |
| WO | WO 03/022330 A2 | 3/2003 |
| WO | 2004/069301 A2 | 8/2004 |
| WO | WO 2007/111519 A1 | 10/2007 |

OTHER PUBLICATIONS

Extended European Search Report dated Apr. 26, 2013, issued by the European Patent Office in corresponding European Patent Application No. 10820338.1-1662/2484400. (6 pages).

* cited by examiner

SYRINGE NEEDLE ASSEMBLY AND MEDICATION INJECTION DEVICE

TECHNICAL FIELD

The present invention relates to an injection needle assembly (i.e. a syringe needle assembly) and a drug injection device (i.e., a medication injection device) in which the surface of a needle tip of a needle tube is coated with a coating agent.

BACKGROUND ART

Conventionally, in order to perform a stable puncture and reduce the pain caused by the puncture, a coating agent, such as silicone resin, fluorine resin or the like, is coated onto the surface of a needle tip of a needle tube. Further, by coating the coating agent onto the surface of the needle tip, the roughness of the tip-end portion of the needle tube is reduced. Therefore, it is possible to reduce the friction between the skin and the needle tube caused in use, reduce the pain caused by the puncture, and perform a stable puncture to the skin.

For example, Patent document 1 describes an art in which a quartz film, which is chemically neutral and stable, is used as the coating agent applied to the surface of the needle tip of the needle tube.

PRIOR ART DOCUMENTS

Patent Documents

[Patent document 1] Japanese Unexamined Patent Application Publication No. H09-108351

DISCLOSURE OF THE INVENTION

Problems to be Solved by the Invention

However, in a conventional injection needle assembly, the needle tube is fixed to the needle hub by using an adhesive in a state where the needle tube has been inserted through a through-hole formed in the needle hub. For this reason, a space is provided between the needle tube and the needle hub for injecting the adhesive therein. Further, the coating is applied to the needle tip of the needle tube after the needle tube has been fixed to the needle hub. Therefore, there is concern that, when coating the coating agent onto the surface of the needle tip of the needle tube, the coating agent might be infiltrated into the clearance between the needle tube and the needle hub by capillarity. Consequently, there is a problem that, in the conventional injection needle assembly, since the coating agent is infiltrated into the clearance between the needle tube and the needle hub, an adverse influence will be exerted on the adhesive that adheres the needle tube to the needle hub, so that the adhesive strength between the needle tube and the needle hub will be reduced.

Further, in an injection needle assembly used for injecting a vaccine or the like into the upper layer of the skin, since the length of the needle tip protruded from the needle hub is set smaller than that of a general injection needle assembly, the coating agent is more easily to be infiltrated into the clearance between the needle tube and the needle hub than a general injection needle assembly, and that is a problem.

In view of the aforesaid problems, it is an object of the present invention to provide an injection needle assembly and a drug injection device capable of preventing the coating agent applied to the surface of the needle tube from being infiltrated into the clearance between the needle tube and needle hub.

Means for Solving the Problems

To solve the above problems, an injection needle assembly according to an aspect of the present invention includes a needle tube that has a needle tip capable of puncturing a living body and that is coated with a coating agent on the surface of a tip-end portion on the side of the needle tip, and a needle hub adapted to hold the needle tube in a state where the needle tip of the needle tube is protruded. The needle hub has a through-hole through which the needle tube is inserted, and a discharge hole extending from the through-hole to the outer surface of the needle hub and adapted to discharge the coating agent infiltrated into the through-hole.

Further, a drug injection device according to another aspect of the present invention includes a needle tube that has a needle tip capable of puncturing a living body and that is coated with a coating agent on the surface of a tip-end portion on the side of the needle tip, a needle hub adapted to hold the needle tube in a state where the needle tip of the needle tube is protruded, and a syringe connected to the needle hub. The needle hub has a through-hole through which the needle tube is inserted, and a discharge hole extending from the through-hole to the outer surface of the needle hub and adapted to discharge the coating agent infiltrated into the through-hole.

Advantages of the Invention

With the injection needle assembly and the drug injection device according to the present invention, by forming the discharge hole for discharging the extra coating agent in the needle hub, it is possible to prevent the coating agent from being infiltrated into the through-hole when coating the coating agent on the needle tip of the needle tube. As a result, since the coating agent can be prevented from contacting the adhesive adhered to the needle tube and the needle hub, the needle tube can be prevented from being dropped off from the needle hub.

BEST MODES FOR CARRYING OUT THE INVENTION

An injection needle assembly and a drug injection device according to an embodiment of the present invention will be described below with reference to FIGS. 1 to 5. Note that, in the drawings, like components are denoted by like numerals. Further, the present invention is not limited to the embodiment described below.

The description will be made in the following order.
1. Configuration examples of injection needle assembly and drug injection device
2. Assembly of injection needle assembly and drug injection device
  2-1. Assembly of injection needle assembly
  2-1. Assembly of drug injection device
3. Method of using drug injection device

1. Configuration Examples of Injection Needle Assembly and Drug Injection Device

Drug Injection Device

An injection needle assembly and a drug injection device according to an embodiment (referred to as "the present embodiment" hereinafter) of the present invention will be described below with reference to FIG. 1 and FIG. 2.

Figure 1:
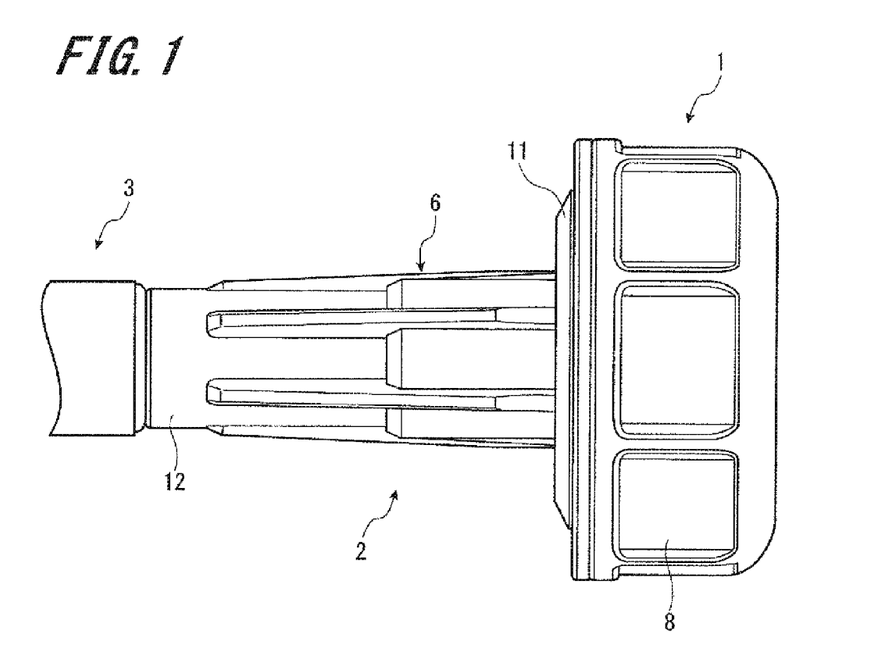
FIG. 1 is a side view showing a drug injection device according to an embodiment of the present invention.
Figure 2:
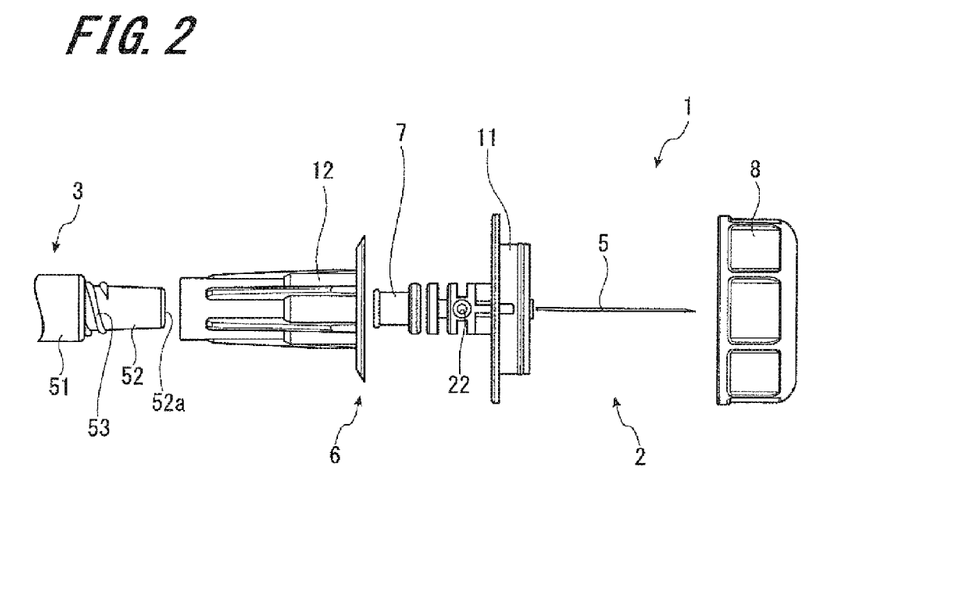
FIG. 2 is an exploded view of the drug injection device according to the aforesaid embodiment.

FIG. 1 is a side view of the drug injection device of the present embodiment, and FIG. 2 is an exploded view of the drug injection device of the present embodiment.

A drug injection device 1 is used for sticking a needle tip into the skin from the skin surface to thereby inject a drug into the upper layer of the skin. The drug injection device 1 includes an injection needle assembly 2, and a syringe 3 detachably connected to the injection needle assembly 2.

Skin is composed of three layers: epidermis, dermis and subcutaneous tissue. The epidermis is a layer of about 50-200 μm from the skin surface, and the dermis is a layer of about 1.5-3.5 mm continuing from the epidermis. Since influenza vaccine is generally subcutaneously or intramuscularly administered, it is administered to the lower layer of the skin or the portion deeper than the lower layer.

On the other hand, it is considered to reduce the dose of the influenza vaccine by administering the influenza vaccine to the upper layer of skin as a target site where many immunocompetent cells are present. Incidentally, the upper layer of skin refers to the epidermis and the dermis of the skin.

As shown in FIG. 2, the injection needle assembly 2 includes a hollow needle tube 5 having a needle hole, a needle hub 6 to which the needle tube 5 is fixed, an elastic member 7 arranged in the needle hub 6, and a cap 8 detachably attached to the needle hub 6. Further, the needle hub 6 includes a first member 11, which is a holding portion for holding the needle tube 5, and a second member 12, which is a connecting portion to which the syringe 3 is connected.

Next, the aforesaid components of the drug injection device 1 will be described below with reference to FIGS. 3 and 4.

Figure 3:
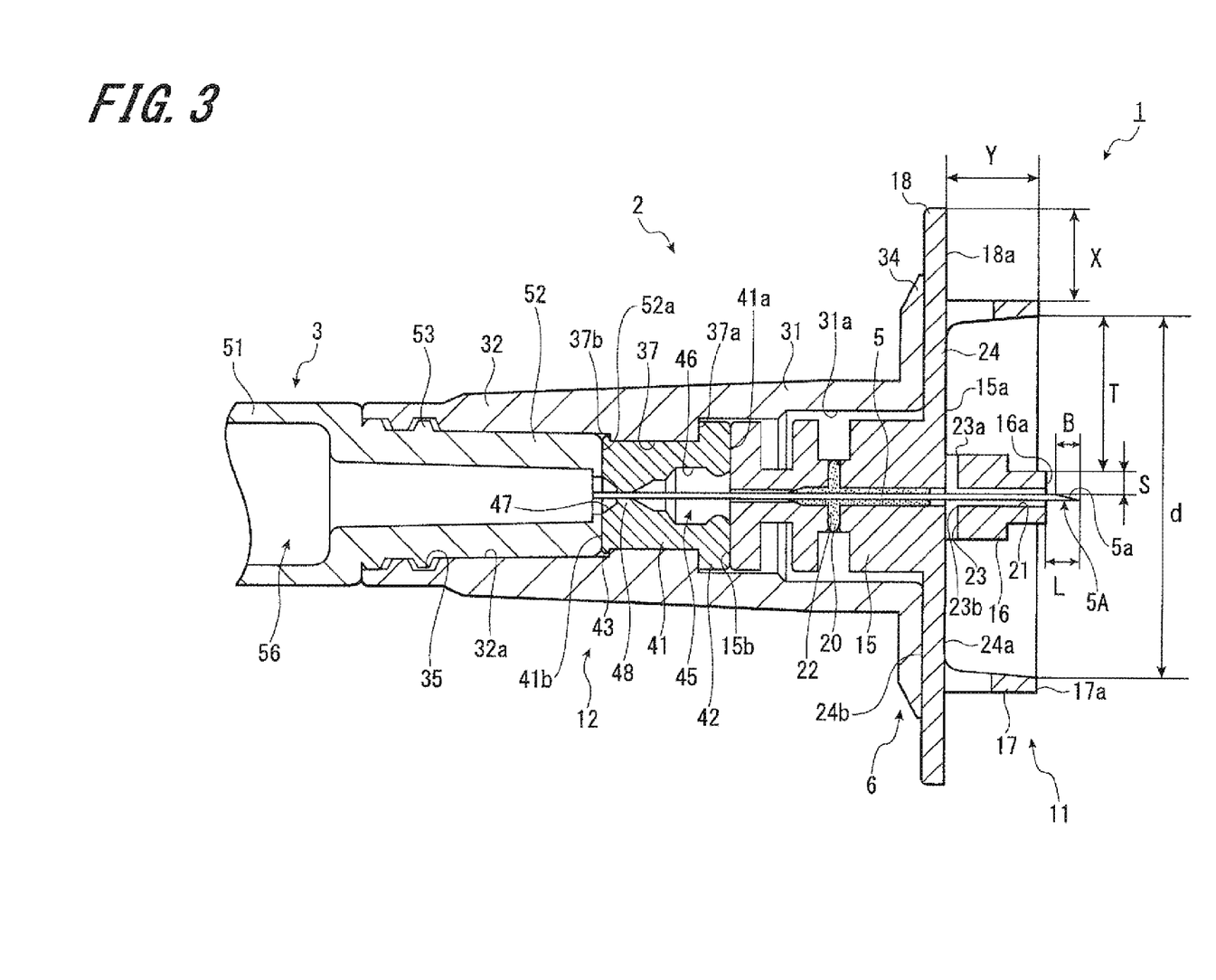
FIG. 3 is a cross section of an injection needle assembly according to the aforesaid embodiment.
Figure 4:
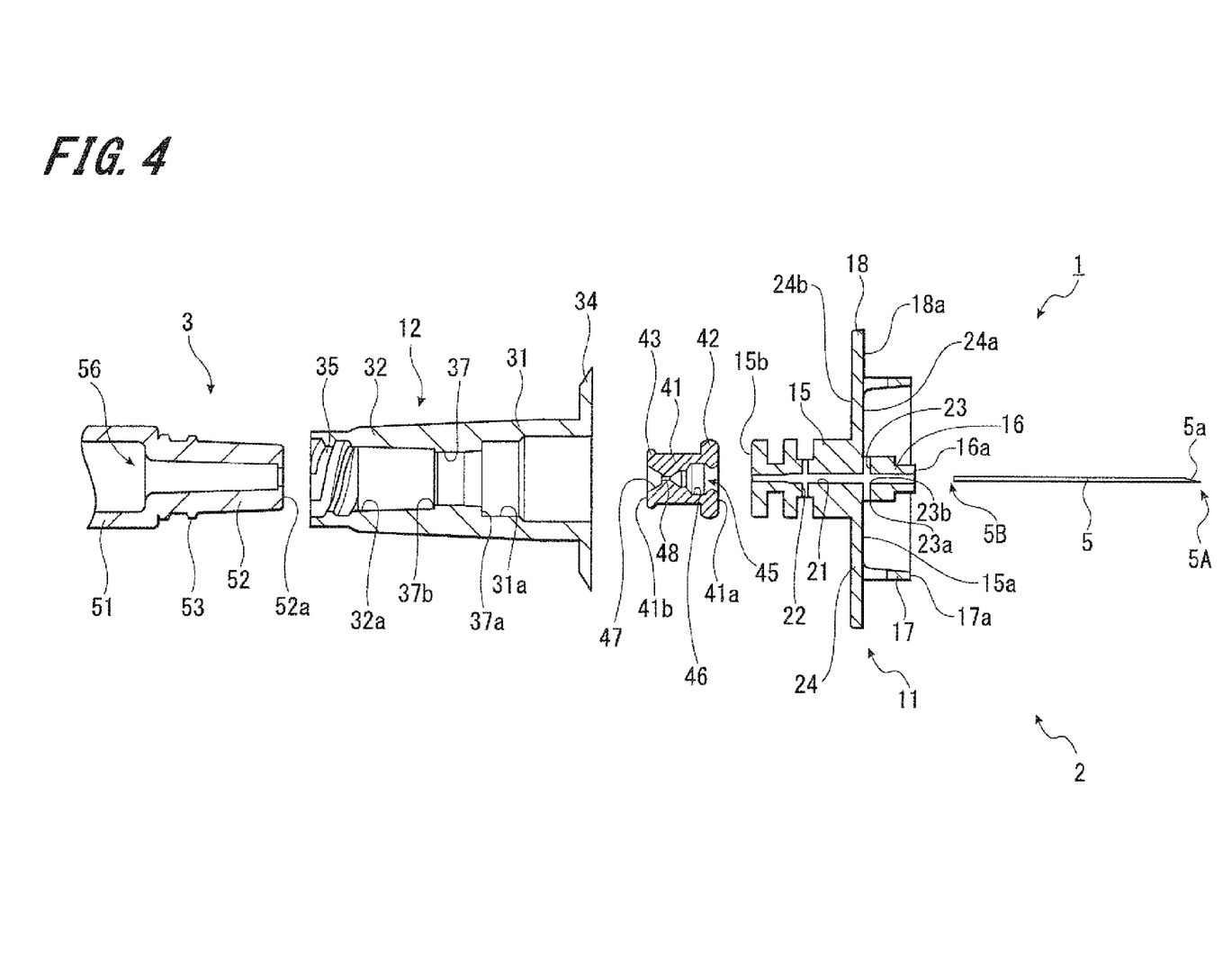
FIG. 4 is an exploded perspective view of the injection needle assembly according to the aforesaid embodiment.

FIG. 3 is a cross section of the drug injection device 1. FIG. 4 is an exploded perspective view of the drug injection device 1.

Injection Needle Assembly

A needle tube of 22-33 gauge (outer diameter: 0.2-0.7 mm) according to ISO standard for medical needle tubes (ISO9626: 1991/Amd. 1:2001(E)) can be used as the needle tube 5 of the injection needle assembly 2. Incidentally, when being used to perform administration to the upper layer of the skin, a needle tube of 26-33 gauge, preferably 30-33 gauge, can be used as the needle tube 5 of the injection needle assembly 2.

A needle tip 5A having a blade face 5a is provided on one end of the needle tube 5. The other end of the needle tube 5, on the side opposite to the needle tip 5A, will be referred to as a "base end 5B" hereinafter. The length of the blade face 5a in the axial direction of the needle tube 5 (referred to as "bevel length B" hereinafter) may be equal to or less than 1.4 mm (which is the minimum thickness of the upper layer of the skin of an adult, which is to be described later), but equal to or greater than about 0.5 mm, which is the bevel length when a short bevel is formed in a needle tube of 33 gauge. In other words, it is preferred that the bevel length B is set in a range of 0.5-1.4 mm.

It is further preferred that the bevel length B is equal to or less than 0.9 mm (which is the minimum thickness of the upper layer of the skin of a child), i.e., it is further preferred that the bevel length B is set in a range of 0.5-0.9 mm. Incidentally, the term "short bevel" means a blade face forming an angle of 18-25° with respect to the longitudinal direction of the needle, which is generally used as an injection needle. Further, a coating agent, such as silicone resin, fluorine resin or the like, is applied to the surface of the needle tip 5A of the needle tube 5. Therefore, it is possible to reduce the friction between the skin and the needle tube caused when puncturing the living body with the needle tube 5, so that it is possible to reduce the pain caused by the puncture.

The material of the needle tube 5 may be, for example, a stainless steel; however, instead of being limited to the stainless steel, the material of the needle tube 5 may also be other metal such as aluminum, aluminum alloy, titanium, titanium alloy, or the like. Further, not only a straight needle, but also a tapered needle in which at least a portion thereof is tapered may be used as the needle tube 5. The tapered needle may have a configuration in which the diameter of a base end portion of the needle is larger than the diameter of a tip end portion of the needle, and a middle portion of the needle has a taper structure. Further, the shape of the cross section of the needle tube 5 may also be a polygonal shape such as a triangular shape, instead of being limited to a circular shape. The needle tube 5 is fixed to the needle hub 6.

Needle Hub

Next, the needle hub 6 will be described below. The first member 11 and the second member 12 of the needle hub 6 are formed separately from each other; however, the first member 11 and the second member 12 may also be integrally formed. Examples of the material of the first member 11 and the second member 12 include synthetic resin such as polycarbonate, polypropylene, polyethylene or the like.

The first member 11 includes a substantially cylindrical base portion 15, an adjusting portion 16, a stabilizer 17, and a guide portion 18. The base portion 15 has two end faces 15a, 15b each perpendicular to the axial direction. The adjusting portion 16 is arranged in the central portion of the end face 15a on one end side in the axial direction of the base portion 15, and is formed as a cylindrical projection projected in the axial direction of the base portion 15. The axis of the adjusting portion 16 and the axis of the base portion 15 coincide with each other.

A through-hole 21, through which the needle tube 5 is inserted, is formed in the axes of the base portion 15 and the adjusting portion 16. An injection hole 22 for injecting an adhesive 20 (see FIG. 3) into the through-hole 21 (see FIGS. 2 and 4) is formed in the base portion 15. The injection hole 22 is opened to the outer circumferential surface of the base portion 15, and is in communication with the through-hole 21 so that the injection hole 22 is substantially perpendicular to the through-hole 21. In other words, the needle tube 5 is fixed to the base portion 15 by the adhesive 20 injected from the injection hole 22 into the through-hole 21.

Further, the adjusting portion 16 is provided with a discharge hole 23 for discharging the coating agent infiltrated into the through-hole 21 through the needle tube 5. The discharge hole 23 is formed in such a manner that it communicates with the through-hole 21 from the outer surface of the adjusting portion 16. The axis of the discharge hole 23 is substantially perpendicular to the axis of the through-hole 21. The discharge hole 23 has an outlet 23a formed on the outer wall of the adjusting portion 16, and an inlet 23b in communication with the through-hole 21.

With such arrangement, when coating the coating agent, such as the as silicone resin, fluorine resin or the like, on the needle tip 5A of the needle tube 5, the coating agent can be prevented from being infiltrated to the side of the base portion 15 through the through-hole 21 formed in the adjusting portion 16. As a result, it is possible to prevent the coating agent from contacting the adhesive 20 that fixes the needle tube 5 to the base portion 15, so that it is possible to prevent the reduction of the adhesive strength between the needle tube 5 and the base portion 15.

Incidentally, although the present embodiment is described based on an example in which the discharge hole 23 penetrates through the adjusting portion 16 in a direction perpendicular to the axial direction of the through-hole 21, the present invention is not limited to this example. The same object may also be achieved if the discharge hole 23 is a recessed portion opened from the outer surface of the adjusting portion 16 to the through-hole 21.

Further, although the present embodiment is described based on an example in which the discharge hole 23 is formed in the adjusting portion 16, the discharge hole 23 may also be formed in the base portion 15 of the first member 11 as long as the discharge hole 23 is formed in a position closer to the blade face 5a of the needle tube 5 than the injection hole 22 to which the adhesive 20 is injected. Further, the discharge hole 23 may also be formed at a plurality of places of the first member 11.

The side of the base end 5B of the needle tube 5 is protruded from the end face 15b, which is the other end in the axial direction of the base portion 15. The base portion 15 is inserted into the second member 12 from the side of the end face 15b, and the side of the base end 5B of the needle tube 5 is inserted through an insertion hole 45 (which is to be described later) of the elastic member 7. The end face 15b of the base portion 15 abuts an end face 41a (which is to be described later) of the elastic member 7.

A connection piece 24 is provided on the outer circumferential surface of the base portion 15. The connection piece 24 is formed as a ring-like flange protruded outward in the radial direction of the base portion 15, and includes two flat surfaces 24a, 24b opposed to each other in the axial direction of the base portion 15. The second member 12 is connected to the flat surface 24b of the connection piece 24. The tip-end portion of the connection piece 24 is the guide portion 18. The details of the guide portion 18 will be described later.

The end face of the adjusting portion 16 is a needle-protruding surface 16a from which the side of the needle tip 5A of the needle tube 5 is protruded. The needle-protruding surface 16a is formed as a flat surface perpendicular to the axial direction of the needle tube 5. When the needle tube 5 is stuck into the upper layer of the skin, the needle-protruding surface 16a contacts the surface of the skin, so that the insertion depth of the needle tube 5 into the upper layer of the skin is regulated. In other words, the insertion depth of the needle tube 5 into the upper layer of the skin is determined by the length of the needle tube 5 protruding from the needle-protruding surface 16a (such length will be referred to as "protruding length L" hereinafter).

The thickness of the upper layer of the skin corresponds to the depth from the surface of the skin to the dermis layer, which is generally in a range of 0.5-3.0 mm. Therefore, the protruding length L of the needle tube 5 can be set in a range of 0.5-3.0 mm.

The vaccine is generally administered to the upper arm; however, when considering administering the vaccine to the upper layer of the skin, more appropriate portion to be stuck will be the portion around the shoulder where the skin is thick, especially the portion of the deltoid muscle. Therefore, the thickness of the upper layer of the skin overlying the deltoid muscle was measured for 19 children and 31 adults. The measurements were performed by imaging the upper layer of skin having high ultrasonic reflectivity using an ultrasonic measurement device (NP60R-UBM High Resolution Echo for Small Animal, NEPA GENE, CO., LTD.). Incidentally, since the measured values showed lognormal distribution, the range of MEAN±2 SD was obtained by taking the geometrical mean.

The results showed that the thickness of the upper layer of skin overlying the deltoid muscle of a child was 0.9-1.6 mm. Further, the results also showed that the thickness of the upper layer of skin overlying the deltoid muscle of an adult was 1.4-2.6 mm in the distal portion, 1.4-2.5 mm in the middle portion, and 1.5-2.5 mm in the proximal portion. It can be confirmed from the above that the thickness of the upper layer of skin overlying the deltoid muscle is equal to or more than 0.9 mm for children, and is equal to or more than 1.4 mm for adults. Consequently, when performing injection on the upper layer of skin overlying the deltoid muscle, it is preferred that the protruding length L of the needle tube 5 is set in a range of 0.9-1.4 mm.

By setting the protruding length L in such a manner, it becomes possible to securely position the blade face 5a of the needle tip 5A in the upper layer of the skin. As a result, the needle hole (the drug solution outlet) opened on the blade face 5a can be positioned in the upper layer of the skin, regardless of its position in the blade face 5a. Incidentally, even when the drug solution outlet is positioned in the upper layer of the skin, if the needle tip 5A is deeply inserted into the upper layer of the skin, the drug solution will flow into the subcutaneous layer from between the side surface of the end portion of the needle tip 5A and the incised skin, and therefore it is important that the blade face 5a is securely positioned in the upper layer of the skin.

Incidentally, when being used to perform administration to the upper layer of the skin, it is difficult to make the bevel length B 1.0 mm or less if the needle tube is larger than 26 gauge. Accordingly, to set the protruding length L of the needle tube 5 in the preferable range (i.e., the range of 0.9-1.4 mm), it is preferred to use a needle tube smaller than 26 gauge.

The needle-protruding surface 16a is formed such that the distance S from the circumferential edge of the needle-protruding surface 16a to the circumferential surface of the needle tube 5 is 1.4 mm or less, preferably in a range of 0.3-1.4 mm. The distance S from the circumferential edge of the needle-protruding surface 16a to the circumferential surface of the needle tube 5 is set considering that a pressure will be applied to the blister formed by administering drug to the upper layer of the skin. In other words, the diameter of the needle-protruding surface 16a is set to sufficiently smaller than the diameter of the blister to be formed in the upper layer of skin, so that the formation of the blister will not be obstructed. As a result, even if the needle-protruding surface 16a presses the skin around the needle tube 5, the administered drug can be prevented from being leaked out.

The stabilizer 17 is formed in a tubular shape protruded from the flat surface 24a of the connection piece 24 provided in the base portion 15. The needle tube 5 and the adjusting portion 16 are arranged in the tube hole of the stabilizer 17. In other words, the stabilizer 17 is formed in a tubular shape covering around the adjusting portion 16 through which the needle tube 5 is penetrated, and is radially spaced from the needle tip 5A of the needle tube 5.

The cap 8 is detachably fitted to the stabilizer 17 (see FIG. 1). The cap 8 covers the needle tip 5A of the needle tube 5. With such arrangement, when mounting the needle hub 6 on the syringe 3, the needle tip 5A can be prevented from being touched by the fingertips and the like of the user. Further, it is possible to constantly keep the used drug injection device 1 or injection needle assembly 2 in a safe condition, and it is possible for the user to dispose the used drug injection device 1 or injection needle assembly 2 without anxiety.

As shown in FIG. 3, an end face 17a of the stabilizer 17 is located closer to the side of the base end 5B of the needle tube 5 than the needle-protruding surface 16a of the adjusting portion 16. When the needle tip 5A of the needle tube 5 sticks the living body, the needle-protruding surface 16a first contacts the surface of the skin, and then the end face 17a of the stabilizer 17 contacts the surface of the skin. At this time, the end face 17a of the stabilizer 17 contacts the surface of the skin, and thereby the drug injection device 1 becomes stable, so that the needle tube 5 can be kept in an attitude where the needle tube 5 is substantially perpendicular to the skin.

Incidentally, the needle tube 5 can be kept in an attitude where the needle tube 5 is substantially perpendicular to the skin even if the end face 17a of the stabilizer 17 is coplanar with the needle-protruding surface 16a or located closer to the side of the needle tip 5A of the needle tube 5 than the needle-protruding surface 16a. Incidentally, considering the raised portion of the skin formed when the stabilizer 17 is pressed against the skin, it is preferred that the distance between the end face 17a of the stabilizer 17 and the needle-protruding surface 16a in the axial direction is set to 1.3 mm or less.

Further, the inner diameter d of the stabilizer 17 is set to a value equal to or larger than the diameter of the blister formed in the skin. To be specific, the distance T between the inner wall of the stabilizer 17 and the circumferential edge of the needle-protruding surface 16a is set in a range of 4-15 mm. With such arrangement, it is possible to prevent the case where the formation of the blister is obstructed due to the pressure applied from the inner wall of the stabilizer 17 to the blister.

The minimal distance T between the inner wall of the stabilizer 17 and the outer circumferential surface of the adjusting portion 16 is set to 4 mm or more, but without upper limit. However, if the distance T is too large, the outer diameter of the stabilizer 17 will become large, and therefore it will be difficult to bring the entire end face 17a of the stabilizer 17 into contact with the skin when the needle tube 5 is to be stuck into the skin of a slender arm, such as an arm a child. Thus, considering the slender arms of children, it is preferred that the distance T is defined to 15 mm as the maximum.

Further, if the distance S between the circumferential edge of needle-protruding surface 16a and the circumferential surface of the needle tube 5 is 0.3 mm or more, the adjusting portion 16 will not enter the skin. Thus, considering the diameter (about 0.3 mm) of the needle-protruding surface 16a and the distance T (4 mm or more) between the inner wall of the stabilizer 17 and the circumferential edge of the needle-protruding surface 16a, the inner diameter d of the stabilizer 17 can be set to 9 mm or larger.

Incidentally, the shape of the stabilizer 17 is not limited to the circular tube shape, but may also be formed, for example, in a polygonal prism shape, such as a quadrangular prism shape, a hexagonal prism shape or the like, having a tube hole formed in the center thereof.

The guide portion 18 is a tip end portion of the connection piece 24 located outside in the radial direction of the first member 11 from the stabilizer 17. The guide portion 18 has a contact surface 18a that contacts the skin. The contact surface 18a is a portion of the flat surface 24a of the connection piece 24, and is a flat surface substantially parallel to the end face 17a of the stabilizer 17. By pressing the stabilizer 17 until the contact surface 18a of the guide portion 18 contacts the skin, the force applied from both the stabilizer 17 and the needle tube 5 for pressing the skin can be constantly maintained at or above a predetermined value, and thereby the protruded portion of the needle tube 5 from the needle-protruding surface 16a (corresponding to the protruding length L) can be securely inserted into the skin.

The length of the distance Y between the contact surface 18a of the guide portion 18 and the end face 17a of the stabilizer 17 (referred to as "guide portion height") is set so that the skin can be pressed and punctured by a suitable pressing force applied from the needle tube 5 and the stabilizer 17. Incidentally, the suitable pressing force of the needle tube 5 and the stabilizer 17 is in a range of, for example, 3N to 20N. As a result, the pressing force applied from the needle tube 5 and the stabilizer 17 to the skin is guided to the user by the guide portion 18, so that the needle tip 5A (the blade face 5a) of the needle tube 5 can be securely positioned in the upper layer of the skin, and it is possible to bring the user a sense of reassurance.

The guide portion height Y is suitably determined based on the inner diameter d of the stabilizer 17 and the length (referred to as "guide portion length" hereinafter) X between the tip end face of the guide portion 18 and the outer circumferential surface of the stabilizer 17. For example, when the inner diameter d of the stabilizer 17 is 12 mm and the guide portion length X is 3.0 mm, the guide portion height Y will be set in a range of 2.3-6.6 mm.

Next, the second member 12 will be described below. The second member 12 is substantially formed in a tubular shape. An end portion in the axial direction of the second member 12 is an insertion portion 31 into which the base portion 15 of the first member 11 is to be inserted, and the other end portion in the axial direction of the second member 12 is a fitting portion 32 for fitting a discharge portion 52 (which is to be described later) of the syringe 3 therein. The size of a tube hole 31a of the insertion portion 31 is set corresponding to the size of the base portion 15 of the first member 11.

The insertion portion 31 is provided with a fixing piece 34, to which the connection piece 24 of the first member 11 is connected. The fixing piece 34 is a ring-like flange formed continuously from the tip end of the insertion portion 31 and protruded outward in the radial direction. The flat surface 24b of the connection piece 24 provided in the first member 11 abuts the fixing piece 34 so as to be fixed. Examples of the method for fixing the fixing piece 34 and the connection piece 24 to each other include: adhesive, ultrasonic welding, laser welding, screw fixation and the like.

The diameter of a tube hole 32a of the fitting portion 32 is set corresponding to the diameter of the discharge portion 52 of the syringe 3, and continuously deceases as going toward the side of the insertion portion 31. A thread groove 35 for screwing the discharge portion 52 of the syringe 3 is formed in the inner surface of the fitting portion 32.

An engaging portion 37, to which the elastic member 7 is engaged, is provided between the insertion portion 31 and the fitting portion 32. The engaging portion 37 is formed as a stepped portion protruded inward in the radial direction from the inner surface of the second member 12, and has two engaging surfaces 37a, 37b each substantially perpendicular to the axial direction of the second member 12. A flange portion 42 (which is to be described later) of the elastic member 7 is engaged with the engaging surface 37a of the engaging portion 37, and a stopper projection 43 of the elastic member 7 is engaged with the engaging surface 37b of the engaging portion 37.

Elastic Member

Next, the elastic member 7 will be described below. The elastic member 7 is arranged inside the second member 12 of the needle hub 6, and is interposed between the first member 11 and the syringe 3. The elastic member 7 includes a body portion 41, the flange portion 42 provided on one end in the axial direction of the body portion 41, and the stopper projection 43 provided the other end of the body portion 41.

The body portion 41 is formed in a substantially cylindrical shape, and has two end faces 41a, 41b each perpendicular to the axial direction. The end face 15b of the base portion 15 of the first member 11 abuts the end face 41a of the body portion 41, and the tip end of the discharge portion 52 of the syringe 3 liquid-tightly abuts the end face 41b of the body portion 41. In other words, the end face 41b is an abutting surface on which the tip end of the discharge portion 52 liquid-tightly abuts.

The body portion 41 is formed with an insertion hole 45 through which the side of the base end 5B of the needle tube 5 protruded from the end face 15b of the base portion 15 is inserted. The insertion hole 45 extends in the axial direction of the body portion 41, and is opened on both end faces 41a, 41b. The inner surface of body portion 41 is defined by an end face side separated portion 46, an abutting surface side separated portion 47, and an adhesive portion 48.

The end face side separated portion 46 forms the opening of the insertion hole 45 on the end face 41a. The end face side separated portion 46 is spaced from the outer circumferential surface of the needle tube 5, and is formed in a tapered shape so that the diameter of the insertion hole 45 continuously increases as going toward the side of the end face 41a. With such arrangement, the side of the base end 5B of the needle tube 5 protruded from the end face 15b of the base portion 15 can be easily inserted through the insertion hole 45. Incidentally, the end face side separated portion 46 of the insertion hole 45 may also be formed in other shapes, instead of being limited to the tapered shape, as long as such shapes enable the needle tube 5 to be easily inserted through the insertion hole 45.

The abutting surface side separated portion 47 forms the opening of the insertion hole 45 on the end face 41b. The abutting surface side separated portion 47 is spaced from the outer circumferential surface of the needle tube 5, and is formed in a tapered shape so that the diameter of the insertion hole 45 continuously increases as going toward the side of the end face 41b. By providing the abutting surface side separated portion 47 to the elastic member 7, the side of the end face 41b of the body portion 41 is elastically deformed so as to cover the base end 5B of the needle tube 5, so that the needle hole can be prevented from being closed.

Further, instead of being limited to the tapered shape, the abutting surface side separated portion 47 of the insertion hole 45 may also be formed as, for example, a recessed portion which has a diameter larger than the diameter of the adhesive portion 48 and which is spaced from the outer circumferential surface of the needle tube 5. In other words, the abutting surface side separated portion 47 of the insertion hole 45 may also be formed in other shapes as long as such shapes enable the side of the end face 41b of the body portion 41 to be elastically deformed so as to cover the base end 5B of the needle tube 5, so that the needle hole can be prevented from being closed.

The adhesive portion 48 is formed between the end face side separated portion 46 and the abutting surface side separated portion 47. The adhesive portion 48 adheres liquid-tightly to the outer circumferential surface of the needle tube 5. With such arrangement, the drug inside the syringe 3 can be prevented from being penetrated into the side of the first member 11 of the needle hub 6 from between the needle tube 5 and the elastic member 7.

The flange portion 42 is formed in a ring-like shape protruded outward in the radial direction from the outer circumferential surface of the body portion 41. The outer diameter of the flange portion 42 is substantially equal to the outer diameter of the base portion 15 of the first member 11. Thus, one flat surface of the flange portion 42 abuts the engaging surface 37a of the engaging portion 37 arranged in the second member 12, and the other flat surface of the flange portion 42 abuts the end face 15b of the base portion 15 of the first member 11. The elastic member 7 is attached to the needle hub 6 by sandwiching the flange portion 42 with the engaging portion 37 of the second member 12 and the base portion 15 of the first member 11.

Similar to the flange portion 42, the stopper projection 43 is formed in a ring-like shape protruded outward in the radial direction from the outer circumferential surface of the body portion 41. The stopper projection 43 is engaged with the engaging surface 37b of the engaging portion 37 provided in the second member 12. The flange portion 42 and the stopper projection 43 are engaged with the engaging portion 37 of the second member 11, and thereby the movement of the elastic member 7 in the axial direction is locked.

Examples of the material of the elastic member 7 include various kinds of rubber material (such as natural rubber, silicone rubber and the like), various kinds of thermoplastic elastomer (such as polyurethane elastomer, styrene elastomer and the like), and elastic materials each obtained by mixing the aforesaid materials.

Syringe

The syringe 3 includes a flange body 51 and the discharge portion 52 formed continuously from the flange body 51. The flange body 51 is formed as a circular tube. The discharge portion 52 is protruded from one end in the axial direction of the flange body 51, and is formed as a circular tube having an outer diameter smaller than that of the flange body 51. The discharge portion 52 is formed in a tapered shape so that the diameter of the discharge portion 52 continuously decreases as going toward the side of the tip end. An end face 52a (i.e., the tip end) of the discharge portion 52 is a flat surface perpendicular to the axial direction, and liquid-tightly abuts the end face 41b of the elastic member 7. Further, a threaded portion 53 for screwing the second member 12 of the needle hub 6 is formed in the outer circumferential surface of the discharge portion 52.

A gasket (not shown) is housed in the flange body 51. The space inside the flange body 51 is divided into two parts by the gasket. One part of the space communicating with the discharge portion 52, along with the space inside the discharge portion 52, defines a liquid chamber 56. A plunger (not shown) is arranged in the other part of the space inside the flange body 51. The plunger is connected to the gasket, and is protruded from the opening on the other end of the flange body 51. By operating the plunger, the gasket is moved within the flange body 51 in the axial direction, and thereby aspiration of the drug into the liquid chamber 56 and discharge of the drug filled into the liquid chamber 56 are performed.

The material of the flange body 51 and the discharge portion 52 may be a synthetic resin (such as polycarbonate, polypropylene, polyethylene or the like), or a metal (such as stainless steel, aluminum or the like).

2. Assembly of Injection Needle Assembly and Drug Injection Device

A method of assembling the injection needle assembly 2 and the drug injection device having the aforesaid configuration will be described below with reference to FIG. 3 and FIG. 5.

Figure 5:
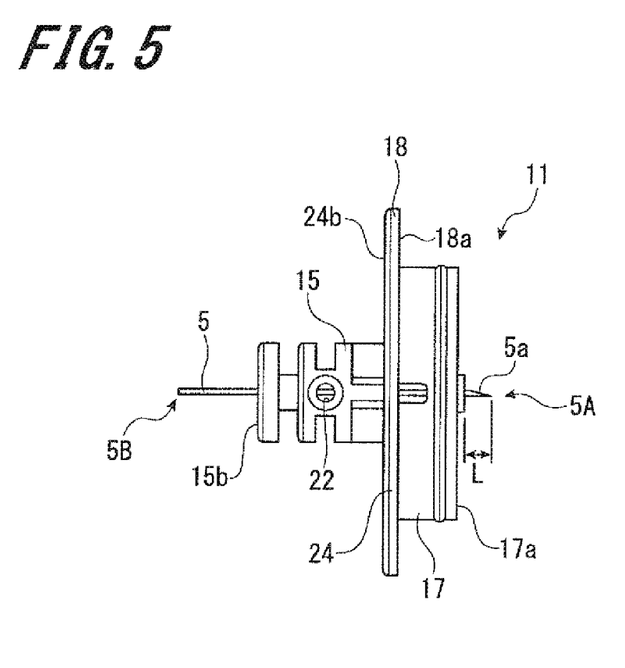
FIG. 5 is a side view showing a first member and a needle tube of the injection needle assembly according to the aforesaid embodiment.

FIG. 5 is a side view showing a state where the needle tube 5 is held by the first member 11.

2-1. Assembly of Injection Needle Assembly

First, as shown in FIG. 5, the needle tube 5 is inserted through the through-hole 21 of the first member 11. At this time, the length of the needle tip 5A of the needle tube 5 protruded from the first member 11 is set in a range of 0.9-1.4 mm, which is smaller than the length of the base end 5B of the needle tube 5 protruded from the first member 11. Next, the adhesive is injected from the injection hole opened on the side surface of the first member 11 to fix the needle tube 5 to the first member 11 (see FIG. 3). Thereby the step of attaching the needle tube 5 is completed; and in such state, the needle tube 5 is held by the first member 11.

Next, a coating agent, such as silicone resin, fluorine resin or the like, is coated on the needle tip 5A of the needle tube 5. At this time, the coating agent is infiltrated into the clearance between the needle tube 5 and the first member 11 by capillarity. However, the adjusting portion 16 is provided with the discharge hole 23 which communicates with the through-hole 21 and which is opened from the outer surface. As a result, the coating agent infiltrated into the through-hole 21 through the needle tube 5 enters the discharge hole 23 from the inlet 23b of the discharge hole 23, and is discharged to the end face 5a of the base portion 15 (which is outer side of the adjusting portion 16) and the flat surface 24a of the connection piece 24 from the outlet 23a of the discharge hole 23. Thus, it is possible to prevent the coating agent from contacting the adhesive, so that it is possible to prevent the reduction of the adhesive strength between the needle tube 5 and the first member 11.

Next, the second member 12, to which the elastic member 7 has been previously engaged, is connected to the first member 11 which holds the needle tube 5. In other words, the base portion 15 of the first member 11 and the side of the base end 5B of the needle tube 5 are inserted into the insertion portion 31 of the second member 12, so that the connection piece 24 of the first member 11 abuts the fixing piece 34 of the second member 12. At this time, the side of the base end 5B of the needle tube 5 is inserted through the insertion hole 45 of the elastic member 7 arranged inside the second member 12, and adhered liquid-tightly to the adhesive portion 48 (see FIG. 3). Thereafter, the fixing piece 34 of the second member 12 is fixed to the connection piece 24 of the first member 11 by a fixing method such as adhesive, ultrasonic welding, laser welding, screw fixation or the like. By the aforesaid steps, the assembly of the injection needle assembly 2 is completed.

Incidentally, the method of assembling the injection needle assembly 2 is not limited to the aforesaid method. For example, the first member 11 and the second member 12 may also be connected to each other after the elastic member 7 has been attached to the base end 5B of the needle tube 5 held on the first member 11.

2-2. Assembly of Drug Injection Device

Next, the assembly of the drug injection device, i.e., the method of mounting the injection needle assembly 2 to the syringe 3, will be described below. In order to mount the injection needle assembly 2 to the syringe 3, first the discharge portion 52 of the syringe 3 is inserted into the fitting portion 32 of the injection needle assembly 2. Thereafter, the threaded portion 53 of the discharge portion 52 is screwed with the thread groove 35 of the fitting portion 32. By the aforesaid steps, the injection needle assembly 2 is mounted to the syringe 3, and thereby the assembly of the drug injection device 1 is completed.

3. Method of Using Drug Injection Device

Next, the method of using the drug injection device 1 will be described below. In order to stick the needle tip 5A of the needle tube 5 into the living body, first the end face 17a of the stabilizer 17 is caused to face the skin. Thereby the needle tip 5A of the needle tube 5 faces the skin to be stuck. Next, the drug injection device 1 is moved substantially perpendicular to the skin, so that the needle tip 5A is stuck into the skin while the end face 17a of the stabilizer 17 is pressed against the skin. At this time, the needle-protruding surface 16a contacts the skin so that the skin can be flatly deformed, while the needle tip 5A of the needle tube 5 can be inserted into the skin by a depth equivalent to the protruding length L.

Next, the end face 17a of the stabilizer 17 is pressed until the contact surface 18a of the guide portion 18 contacts the skin. Here, the value of the guide portion height y (see FIG. 3) is set so that the skin can be stuck by a suitable pressing force applied from the needle tube 5 and the stabilizer 17. Thus, the force of the stabilizer 17 for pressing against the skin becomes a predetermined value.

As a result, the suitable pressing force of the stabilizer 17 can be recognized by the user, and the needle tip 5A and the blade face 5a of the needle tube 5 can be securely positioned in the upper layer of the skin. In such a manner, the guide portion 18 becomes a landmark for recognizing the suitable pressing force of the stabilizer 17, and thereby the user can use the drug injection device 1 with a sense of reassurance.

Further, since the stabilizer 17 abuts the skin, the attitude of the drug injection device 1 becomes stable, so that it is possible to stick the needle tube 5 straight into the skin. Further, after the needle tip has been stuck into the skin, waggling caused in the needle tube 5 can be prevented, and therefore the drug can be administered stably. In the case of a needle tube with a very short protruding length of about 0.5 mm, for example, there is a possibility that the needle tip will not be inserted into the skin even if the needle tip is brought into contact with the skin. However, since the skin is pressed down perpendicularly by the stabilizer 17, the skin inside the stabilizer 17 is strained so as to be in a tensioned state. Thus, since the skin becomes hard to flee from the needle tip 5A of the needle tube 2, the stabilizer 17 has an effect of making it easier for the needle tip 5A to stick the skin.

After the side of the needle tip 5A of the needle tube 5 has stuck into the skin, the plunger (not shown) is pressed, so that the gasket (not shown) is moved toward the side of the discharge portion 52. Thus, the drug filled in the liquid chamber 56 of the syringe 3 is pushed out from the discharge portion 52 and injected into the upper layer of the skin from the needle tip 5A through the needle hole of the needle tube 5. At this time, since a space is formed between the tip end of the discharge portion 52 and the base end 5B of the needle tube 5, the residual amount of the drug can be reduced.

It is to be understood that the present invention is not limited to the embodiment described above and shown in the attached drawings, and various modifications can be made without departing from the spirit and scope of the present invention. For example, although the present embodiment is described based on an example in which an elastic member is provided between the first member and the second member, the injection needle assembly may be configured without the elastic member, or the second member and the elastic member may be integrally formed.

EXPLANATION OF REFERENCE NUMERALS 1 drug injection device
2 injection needle assembly
3 syringe
5 needle tube
5A needle tip
5b base end
5a blade face
6 needle hub
7 elastic member
11 first member
12 second member
15 base portion
16 adjusting portion
16a needle-protruding surface
17 stabilizer
18 guide portion
20 adhesive
21 through-hole
22 injection hole
23 discharge hole
23a outlet
23b inlet
24 connection piece
L protruding length
S distance from the circumferential edge of the needle-protruding surface to the circumferential surface of the needle tube
T distance between the inner wall of the stabilizer and the outer circumferential surface of the adjusting portion
x guide portion length
y guide portion height
d inner diameter

The invention claimed is:
1. An injection needle assembly comprising:
a needle tube that has a needle tip capable of puncturing a living body and that is coated with a coating agent on the surface of a tip-end portion on the side of the needle tip; and
a needle hub adapted to hold the needle tube in a state where the needle tip of the needle tube is protruded, the needle hub possessing a side surface,
wherein the needle hub has a through-hole through which the needle tube is inserted, and a discharge hole extending from the through-hole to the outer surface of the needle hub and adapted to discharge the coating agent infiltrated into the through-hole,
wherein the needle hub has an injection hole formed on the side surface thereof, the injection hole communicating with the through-hole and being adapted to inject an adhesive therein, and
wherein the discharge hole is formed at a position closer to the side of the needle tip of the needle tube than the injection hole.
2. The injection needle assembly according to claim 1, wherein the discharge hole comprises a plurality of discharge holes formed in the needle hub.
3. The injection needle assembly according to claim 1, wherein the needle hub has an adjusting portion arranged around the needle tube, the adjusting portion having a needle-protruding surface from which the needle tip of the needle tube is protruded.
4. The injection needle assembly according to claim 1, wherein the needle hub has a stabilizer arranged to cover around the needle tube in a state where the needle tip of the needle tube is protruded, the stabilizer having an end face which contacts the skin when the needle tube punctures the living body.
5. The injection needle assembly according to claim 1, wherein the needle hub has two axial ends,
wherein a first length of the needle tube protrudes from one axial end of the needle hub and a second length of the needle tube protrudes from the other axial end of the needle hub, and
wherein the first length is smaller than the second length.
6. The injection needle assembly according to claim 1, wherein the needle tube is in a range of 26 to 33 gauge.
7. A drug injection device comprising:
a needle tube that has a needle tip capable of puncturing a living body and that is coated with a coating agent on the surface of a tip-end portion on the side of the needle tip;
a needle hub adapted to hold the needle tube in a state where the needle tip of the needle tube is protruded, the needle hub possessing a side surface; and
a syringe connected to the needle hub,
wherein the needle hub has a through-hole through which the needle tube is inserted, and a discharge hole extending from the through-hole to the outer surface of the needle hub and adapted to discharge the coating agent infiltrated into the through-hole,
wherein the needle hub has an injection hole formed on the side surface thereof, the injection hole communicating with the through-hole and being adapted to inject an adhesive therein, and
wherein the discharge hole is formed at a position closer to the side of the needle tip of the needle tube than the injection hole.

* * * * *